United States Patent
Yamagishi et al.

(10) Patent No.: US 6,885,200 B2
(45) Date of Patent: Apr. 26, 2005

(54) MEASURING APPARATUS, PURITY CONTROLLER, AND MIXING RATIO CONTROLLER FOR INSULATIVE FLUID

(75) Inventors: Junichi Yamagishi, Tokyo (JP); Eikou Yo, Tokyo (JP)

(73) Assignee: Unirec Co., Ltd., Tokyo (JP)

(*) Notice: Subject to any disclaimer, the term of this patent is extended or adjusted under 35 U.S.C. 154(b) by 2 days.

(21) Appl. No.: 10/393,898

(22) Filed: Mar. 21, 2003

(65) Prior Publication Data

US 2003/0184316 A1 Oct. 2, 2003

(30) Foreign Application Priority Data

Mar. 27, 2002 (JP) .................................... P2002-087431

(51) Int. Cl.[7] .............................................. G01R 27/26
(52) U.S. Cl. ..................................... 324/663; 324/658
(58) Field of Search ................................ 324/663, 658, 324/664, 665, 672; 73/304 R, 304 C

(56) References Cited

U.S. PATENT DOCUMENTS 4,487,057 A     12/1984  Lutz .......................... 73/40.5 R
5,330,783 A  *  7/1994   Saidman et al. .................. 427/8
5,423,206 A     6/1995   Hetzel ........................ 73/61.77
5,790,422 A  *  8/1998   Power et al. ............. 73/304 R

FOREIGN PATENT DOCUMENTS

JP              10-209108           8/1998

* cited by examiner

Primary Examiner—N. Le
Assistant Examiner—John Teresinski
(74) Attorney, Agent, or Firm—Jordan and Hamburg LLP

(57) ABSTRACT

A measuring apparatus correctly measures the purity, mixing ratio, and the like of an insulative (nonconductive) fluid such as ultrapure water flowing through a passage.

The apparatus includes first to third sensors (19, 21, 23) to detect capacitance changes on the passage (1a) covered with an insulating resin pipe, a memory (41) to store reference capacitance changes, and a controller (35) to compare the detected capacitance changes with the stored reference capacitance changes, measure a purity of the insulative fluid flowing through the passage, and control the purity of the insulative fluid.

5 Claims, 9 Drawing Sheets

MEASURING APPARATUS, PURITY CONTROLLER, AND MIXING RATIO CONTROLLER FOR INSULATIVE FLUID

BACKGROUND OF THE INVENTION

1. Field of the Invention

The present invention relates to a measuring apparatus to measure the purity, mixing ratio, and the like of an insulative (nonconductive) fluid flowing through a passage, a purity controller to control the purity of the insulative fluid according to the measurement, and a mixing ratio controller to control the mixing ratio of the insulative fluid according to the measurement.

2. Description of the Related Art

FIG. 10 shows an example of an apparatus to measure a state of a fluid flowing through a pipe according to a prior art. The prior art inserts electrodes 203 and 205 into the pipe 201 and measures a state of a fluid 207 flowing through the pipe 201. More precisely, the electrodes 203 and 205 detect a conductivity in the pipe 201 and finds a conductivity difference between a clean fluid 209 and foreign matter 211 in the fluid 207. If the foreign matter 211 is found in the fluid 207 according to the detected conductivity difference, the fluid 207 with the foreign matter 211 is branched and discharged, the foreign matter 211 is removed to provide the clean fluid 209.

The prior art of FIG. 11 is unable to detect insulative foreign matter contained in an insulative fluid.

Ultrapure water is an insulative (nonconductive) fluid and is employed to wash semiconductor silicon wafers. After the washing, the used ultrapure water is regenerated and used again for wafer washing. The used ultrapure water contains fine silicon-wafer fragments. If the ultrapure water containing the silicon fragments is used as it is to wash wafers, the surfaces of the wafers will be damaged to deteriorate the yields of semiconductor products. The fragments, therefore, must be removed. To remove the fragments from the used ultrapure water, filters are employed. Before using the regenerated ultrapure water for washing wafers, it is inspected for foreign matter. If foreign matter is detected in the regenerated ultrapure water, the water is again passed through the fillers, and only ultrapure water containing no foreign matter is used for washing wafers.

Ultrapure water and wafer fragments are insulative or nonconductive, and therefore, the prior art of FIG. 11 that measures a conductivity is incapable of detecting silicon fragments in ultrapure water.

To mirror-finish semiconductor silicon wafers, abrasive (slurry) is employed. The slurry is a mixture of ultrapure water and silica particles. The silica is a kind of aluminum ceramics. If a silica concentration in the ultrapure water is low, the slurry will insufficiently mirror-finish the wafers, and if the silica concentration is too high, the slurry will damage mask patterns on the wafers. The silica concentration of the slurry, therefore, must correctly be controlled. The ultrapure water and silica particles are insulative or nonconductive, and therefore, the prior art of FIG. 11 that measures a conductivity is incapable of detecting a concentration of silica particles in ultrapure water.

The slurry is regenerated and repeatedly used, and like the ultrapure water used for washing wafers, the slurry is inspected for foreign matter such as silicon fragments before reuse, so that only slurry containing no foreign matter is used to polish wafers. The prior art of FIG. 11 is unable to detect such foreign matter in slurry due to the same reason mentioned above.

There are other measuring apparatuses employing ultrasonic waves, visible rays, UV monitors, and the like for measuring insulative fluids. These apparatuses suffer from low accuracy, and therefore, are insufficient to increase the yields of wafer processing.

SUMMARY OF THE INVENTION

An object of the present invention is to provide a measuring apparatus capable of correctly measuring the purity, mixing ratio, and the like of an insulative or nonconductive fluid flowing through a passage, a purity controller capable of controlling the purity of the insulative fluid according to the measurement, and a mixing ratio controller capable of controlling the mixing ratio of the insulative fluid according to the measurement.

A first aspect of the present invention provides a measuring apparatus for an insulative fluid, including a capacitance sensor to detect a capacitance change on a passage through which the insulative fluid is flowing, a storage unit to store a reference capacitance change, and a ratio measuring unit to compare the detected capacitance change with the reference capacitance change and determine a ratio related to the insulative fluid flowing through the passage.

For the measuring apparatus of the first aspect, a second aspect of the present invention provides the capacitance sensor with a measuring electrode and a ground electrode. The electrodes are insulated from the passage and wound around the passage.

For the measuring apparatus of the second aspect, a third aspect of the present invention forms the ground electrode narrower than the measuring electrode and alternately arranges the ground electrode and measuring electrode.

For the measuring apparatus of any one of the second and third aspects, a fourth aspect of the present invention spirally winds the measuring electrode and ground electrode around the passage in the fluid flowing direction.

For the measuring apparatus of any one of the first to fourth aspects, a fifth aspect of the present invention allows the ratio measuring unit to measure a purity of the insulative fluid flowing through the passage.

For the measuring apparatus of any one of the first to fourth aspects, a sixth aspect of the present invention allows the ratio measuring unit to measure a mixing ratio of the insulative fluid flowing through the passage.

For the measuring apparatus of the fifth aspect, a seventh aspect of the present invention arranges a filter upstream of the capacitance sensor to remove foreign matter from the insulative fluid flowing through the passage, an outlet and a branch mouth downstream of the filter, an adjuster to switch the flow of the insulative fluid to one of the outlet and branch mouth, and a controller to control the adjuster to switch the flow of the insulative fluid to the outlet if the measured purity is within a set value, and if the measured purity is out of the set value, to the branch mouth.

For the measuring apparatus of the sixth aspect, an eighth aspect of the present invention employs a mixer to mix at least two kinds of insulative fluids with each other and pour the mixed insulative fluids into the passage, an outlet and a branch mouth arranged downstream of the mixer, an adjuster to switch the flow of the mixed insulative fluids to one of the outlet and branch mouth, and a controller to control the adjuster to switch the flow of the mixed insulative fluids to the outlet if the measured mixing ratio is within a set value, and if the measured mixing ratio is out of the set value, to the branch mouth.

The first aspect passes an insulative fluid through the passage and detects a capacitance change on the passage with the use of the capacitance sensor. The storage unit stores a reference capacitance change. The ratio measuring unit compares the detected capacitance change with the reference capacitance change and determines a ratio related to the insulative fluid flowing through the passage.

The first aspect is capable of correctly measuring the ratio of an insulative fluid to insulative foreign matter, or a mixing ratio of two or more kinds of insulative fluids.

In addition to the effects of the first aspect, the second aspect provides the capacitance sensor with a measuring electrode and ground electrode. The second aspect is capable of correctly measuring the ratio of an insulative fluid to insulative foreign matter, or a mixing ratio of two or more kinds of insulative fluids.

In addition to the effects of the second aspect, the third aspect forms the ground electrode narrower than the measuring electrode and alternately arranges the ground electrode and measuring electrode. The third aspect is capable of correctly measuring the ratio of an insulative fluid to insulative foreign matter, or a mixing ratio of two or more kinds of insulative fluids.

In addition to the effects of the second or third aspect, the fourth aspect spirally winds the measuring electrode and ground electrode around the passage in the fluid flowing direction. The fourth aspect is capable of correctly measuring the ratio of an insulative fluid to insulative foreign matter, or a mixing ratio of two or more kinds of insulative fluids.

In addition to the effects of the first to fourth aspects, the fifth aspect employs the ratio measuring unit to correctly measure a purity of the insulative fluid flowing through the passage.

In addition to the effects of the first to fourth aspects, the sixth aspect employs the ratio measuring unit to correctly measure a mixing ratio of the insulative fluid flowing through the passage.

In addition to the effects of the fifth aspect, the seventh aspect employs the filter upstream of the capacitance sensor to remove foreign matter from the insulative fluid flowing through the passage, the outlet and branch mouth downstream of the filter, the adjuster to switch the flow of the insulative fluid to one of the outlet and branch mouth, and the controller to control the adjuster to switch the flow of the insulative fluid to the outlet if the measured purity is within a set value, and if the measured purity is out of the set value, to the branch mouth. The seventh aspect is capable of surely providing only an insulative fluid whose purity is within the set value.

In addition to the effects of the sixth aspect, the eighth aspect employs the mixer to mix at least two kinds of insulative fluids with each other and pour the mixed insulative fluids into the passage, the outlet and branch mouth downstream of the mixer, the adjuster to switch the flow of the mixed insulative fluids to one of the outlet and branch mouth, and the controller to control the adjuster to switch the flow of the mixed insulative fluids to the outlet if the measured mixing ratio is within a set value, and if the measured mixing ratio is out of the set value, to the branch mouth. The eighth aspect is capable of surely providing only an insulative fluid whose mixing ratio is within the set value.

DETAILED DESCRIPTION OF EMBODIMENTS (First Embodiment)

Figure 1:
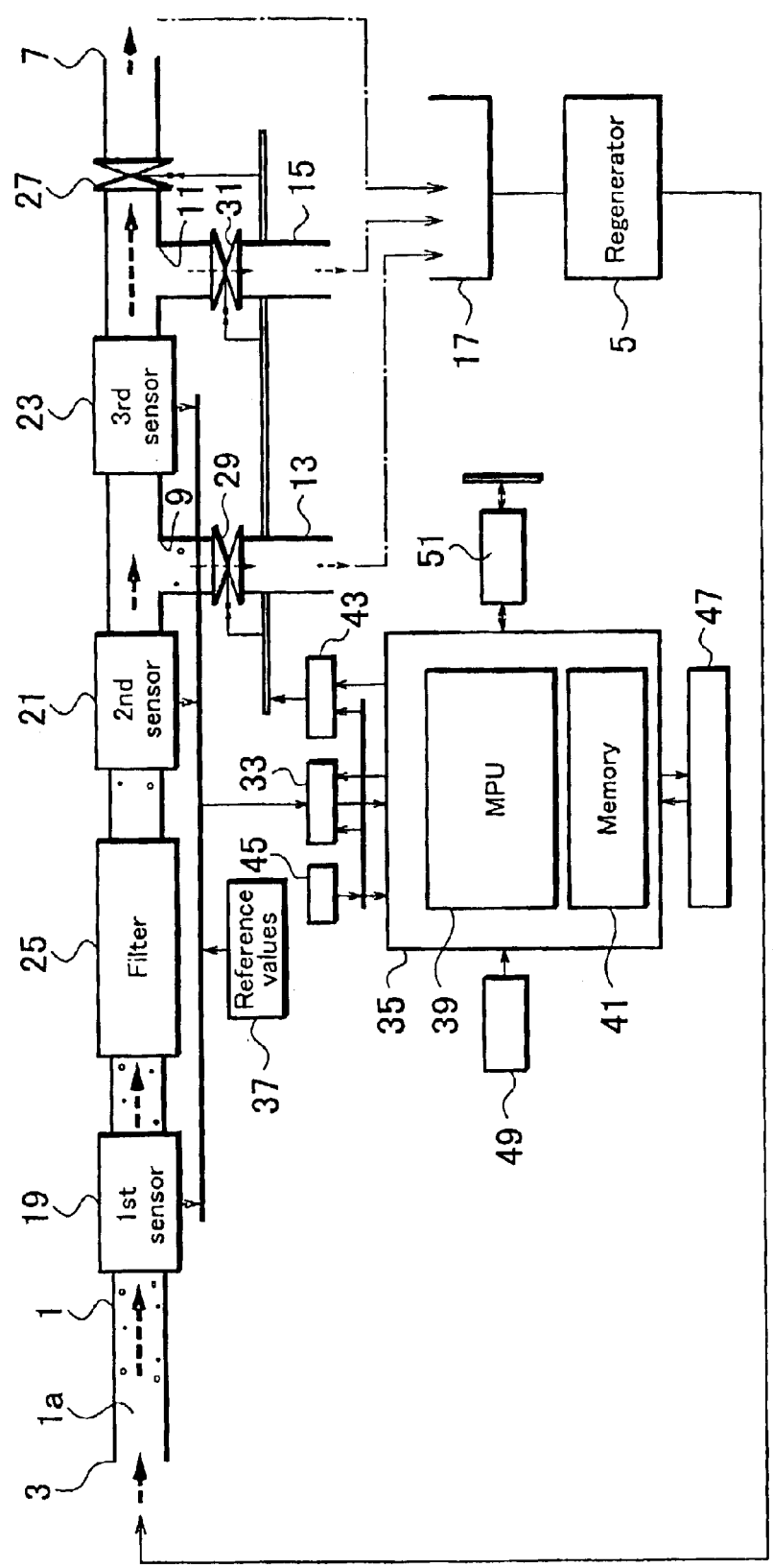
FIG. 1 is a schematic view showing a purity controller for an insulative fluid according to a first embodiment of the present invention.

FIG. 1 is a schematic view showing a purity controller for an insulative (nonconductive) fluid according to the first embodiment of the present invention. A pipe 1 forms a passage 1a to pass an insulative fluid such as ultrapure water for washing semiconductor silicon wafers.

According to the first embodiment, the pipe 1 is made of an insulator, for example, insulative resin such as vinyl chloride. The pipe 1 may be made of the insulator only at locations where first, second, and third sensors 19, 21, and 23 are arranged. The insulator may be quartz glass.

An end 3 of the pipe 1 is connected to a regenerator 5, and the other end of the pipe 1 has an outlet 7. In the vicinity of the outlet 7, the pipe 1 has a first branch mouth 9 and a second branch mouth 11. The first and second branch mouths 9 and 11 are connected to first and second branch pipes 13 and 15, respectively. The first and second branch pipes 13 and 15 are connected to a recycle tank 17. The recycle tank 17 is connected to the regenerator 5. Ultrapure water discharged from the outlet 7 is used to wash semiconductor silicon wafers, and thereafter, is collected into the recycle tank 17.

The pipe 1 has the first to third sensors 19, 21, 23 that are arranged in this order from the upstream side of the pipe 1, to detect capacitance changes on the passage 1a. The second sensor 21 is arranged upstream of the first branch mouth 9. The third sensor 23 is arranged upstream of the second branch mouth 11.

A filter 25 is arranged upstream of the second and third sensors 21 and 23, to remove foreign matter such as silicon wafer fragments from ultrapure water flowing through the passage 1a.

On the downstream side of the pipe 1, there are first to third solenoid valves 27, 29, and 31 serving as adjusters to switch a flow of ultrapure water in the passage 1a to any one of the outlet 7, first branch mouth 9, and second branch mouth 11.

The first solenoid vale 27 is arranged downstream of the second branch mouth 11 in the vicinity of the outlet 7. The first solenoid valve 27 is opened to discharge ultrapure water from the outlet 7 and is closed to stop discharging ultrapure water from the outlet 7.

The second solenoid valve 29 is arranged in the first branch pipe 13. The third solenoid valve 31 is arranged in the second branch pipe 15. If the second solenoid valve 29 is opened with the first and third solenoid valves 27 and 31 closed, ultrapure water in the passage 1a is discharged through the first branch pipe 13 into the recycle tank 17. If the third solenoid valve 31 is opened with the first and second valves 27 and 29 closed, ultrapure water in the passage 1a is discharged through the second branch pipe 15 into the recycle tank 17. If the first solenoid valve 27 is opened with the second and third solenoid valves 29 and 31 closed, the discharging of ultrapure water from the passage 1a to the recycle tank 17 is stopped.

The first to third sensors 19, 21, and 23 provide detected signals through a signal processor 33 to a control unit 35. The control unit 35 beforehand receives reference capacitance changes 37 through the signal processor 33. The reference capacitance changes 37 are detected in advance on the passage 1a by sensors like the sensors 19, 21, and 23.

The reference capacitance changes 37 may include a first reference capacitance change detectable when ultrapure water flowing through the passage 1a contains no gas (bubbles) nor silicon wafer fragments, a second reference capacitance change detectable when the ultrapure water flowing through the passage 1a contains gas (bubbles), and a third reference capacitance change detectable when the ultrapure water flowing through the passage 1a contains silicon wafer fragments. The reference capacitance changes to be used for the present invention are not limited to those mentioned above. Various reference capacitance changes corresponding to various states of an insulative fluid are employable for the present invention.

The control unit 35 includes, for example, an MPU (microprocessor unit) 39 and a memory 41. Instead of the MPU 39, a DSP (digital signal processor) is employable.

The memory 41 stores the reference capacitance changes 37. According to the first embodiment, the memory 41 serves as a storage unit and stores the first to third reference capacitance changes used to determine a ratio related to ultrapure water flowing through the passage 1a.

The control unit 35 serves as a ratio measuring unit that compares a detected capacitance change with the reference capacitance changes stored in the memory 41 and determines a ratio related to ultrapure water flowing through the passage 1a.

Namely, the control unit 35 compares a capacitance change detected by the first sensor 19 with the first to third reference capacitance changes and determines a ratio of gas (bubbles) and silicon wafer fragments contained in ultrapure water flowing through the passage 1a. The control unit 35 compares a capacitance change detected by the second sensor 21 with the first and second reference capacitance changes and determines a ratio of gas (bubbles) contained in the ultrapure water flowing through the passage 1a. The control unit 35 compares a capacitance change detected by the third sensor 23 with the first and third reference capacitance changes and determines a ratio of silicon wafer fragments contained in the ultrapure water flowing through the passage 1a. Consequently, the control unit 35 measures a purity of the ultrapure water flowing through the passage 1a.

The control unit 35 controls the first to third solenoid valves 27, 29, and 31 such that, if the measured purity is within a set value, (be ultrapure water is discharged through the outlet 7, and if the measured purity is out of the set value, through one of the first and second branch mouths 9 and 11. To achieve this, the control unit 35 is connected to the first to third solenoid valves 27, 29, and 31 through a driver 43.

The control unit 35 is also connected to a power source 45, a display panel 47, an ambient sensor 49, and a data transfer interface 51.

Figure 2:
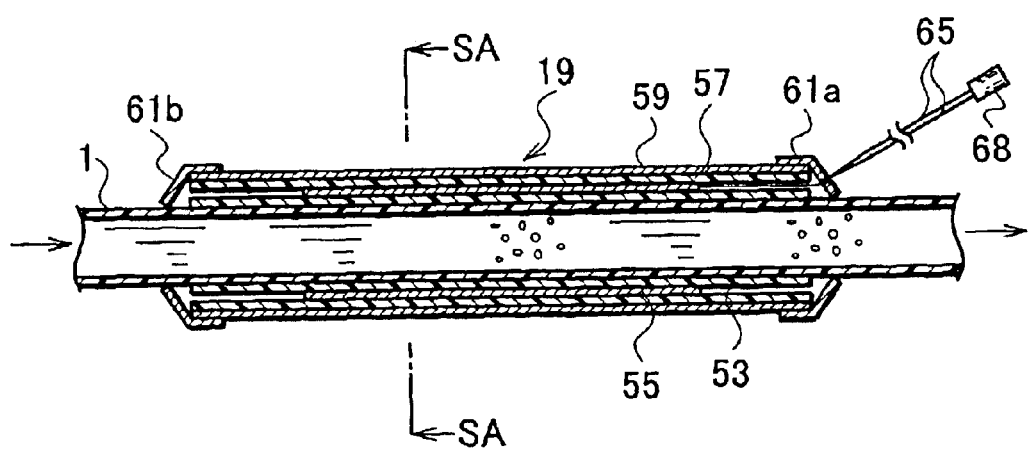
FIG. 2 is a sectional view showing a sensor and the periphery thereof in the apparatus of FIG. 1.
Figure 3:
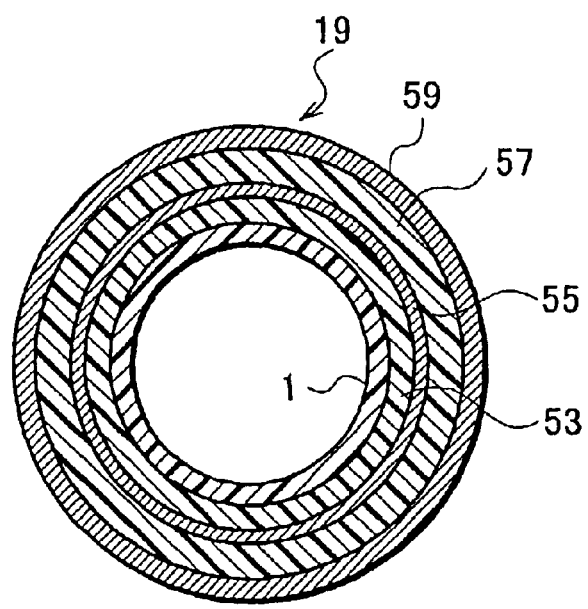
FIG. 3 is an enlarged sectional view taken along a line SA—SA of FIG. 2.
Figure 4:
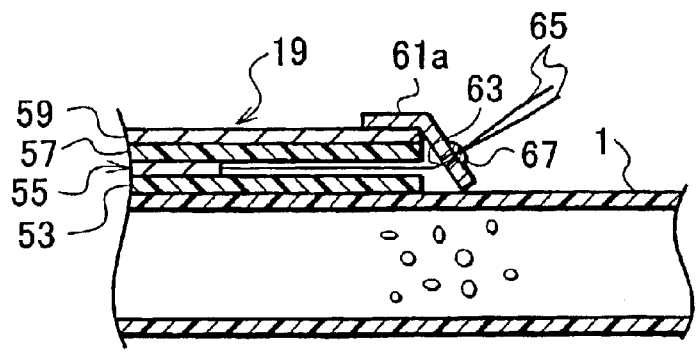
FIG. 4 is an enlarged sectional view showing a part of the sensor of FIG. 2.

FIGS. 2 to 4 show an example of the structure of any one of the first to third sensors 19, 21, and 23.

FIG. 2 is a sectional view showing the sensor and the periphery thereof, FIG. 3 is an enlarged sectional view taken along a line SA—SA of FIG. 2, and FIG. 4 is an enlarged sectional view showing a part of FIG. 2. The first to third sensors 19, 21, and 23 have an identical structure, and therefore, the first sensor 19 will be explained as a representative.

In FIGS. 2 to 4, the first sensor 19 is a capacitance sensor consisting of an electrode 55 made of conductive metal foil wound around the pipe 1. The electrode 55 is insulated from the pipe 1 and includes a measuring electrode 69 and a ground electrode 71.

More precisely, the electrode 55 is wound around a cylinder 53 that is arranged around the pipe 1 forming the passage 1a. According to the first embodiment, the cylinder 53 is made of an insulator such as vinyl chloride. The cylinder 53 may be made of any other insulator, for example, quartz glass or resin. The cylinder 53 is tightly attached around the pipe 1 by, for example, bonding. The cylinder 53 can be formed as an assembly and can easily be attached to the pipe 1.

The electrode 55 is made of conductive metal foil such as copper foil. The electrode 55 is tightly covered with an insulator 57, which is covered with a shield 59. According to the first embodiment, the insulator 57 is a vinyl-chloride pipe. The insulator 57 may be made of, for example, quartz glass or resin.

According to the first embodiment, the shield 59 is an aluminum pipe tightly attached around the insulator 57. End shields 61a and 61b are fixed to both ends of the shield 59. According to the first embodiment, the end shields 61a and 61b are made of aluminum.

The end shield 61a has a through hole 63 as shown in FIG. 4. Through the hole 63, leads 65 of the electrode 55 are guided to the outside. Resin 67 is applied between the end shield 61a and the leads 65. The leads 65 are connected to a connector 68 as shown in FIGS. 2 and 5.

Figure 5:
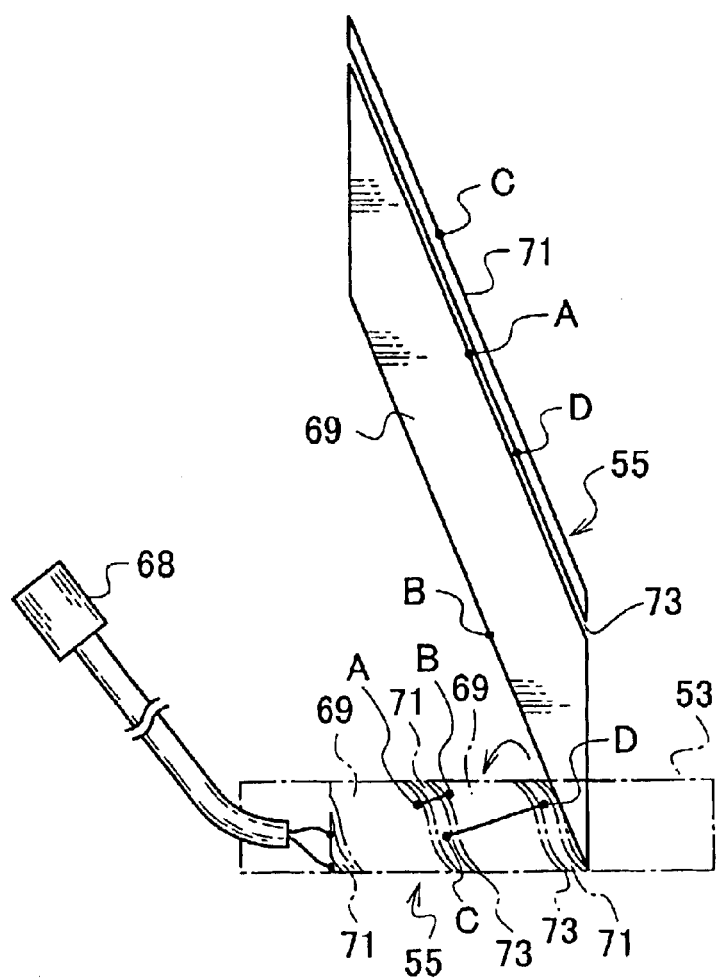
FIG. 5 is an explanatory view showing a winding state of electrodes of the sensor of FIG. 2.

FIG. 5 shows the details of the electrode 55. As indicated with dash-and-dot lines in FIG. 5, the electrode 55 is spirally wound around the cylinder 53. A developed state of the electrode 55 is indicated with continuous lines in FIG. 5. The electrode 55 consists of the measuring electrode 69 and ground electrode 71. In the developed state, the electrodes 69 and 71 are each a parallelogram ribbon made of copper foil. The lengths of short sides (vertical edges depicted with the continuous lines in FIG. 5) of the electrodes 69 and 71 plus the length of a gap 73 between the electrodes 69 and 71 are substantially equal to a circumferential length of the cylinder 53.

The ground electrode 71 is narrower than the measuring electrode 69. The measuring electrode 69 and ground electrode 71 are spirally wound around the cylinder 53 in a fluid flowing direction as indicated with the dash-and-dot lines. The electrodes 69 and 71 are fixed to the cylinder 53 by, for example, bonding. The number of windings of the electrodes 69 and 71 around the cylinder 53 is, for example, three. The number of windings, however, is optional as long as the electrodes 69 and 71 can properly detect capacitance on the pipe 1. Between the electrodes 69 and 71 around the cylinder 53, there is the gap 73.

Around the cylinder 53, the electrodes 69 and 71 are alternately arranged. In the wound state, the adjacent windings of the measuring electrode 69 are short-circuited between points A and B. Similarly, the adjacent windings of the ground electrode 71 are short-circuited between points C and D. In FIG. 5, the short-circuit points A, B, C, and D are on the same plane for the sake of easy understanding. In practice, the points A, B, C, and D are located as shown in the developed view of FIG. 5.

Figure 6:
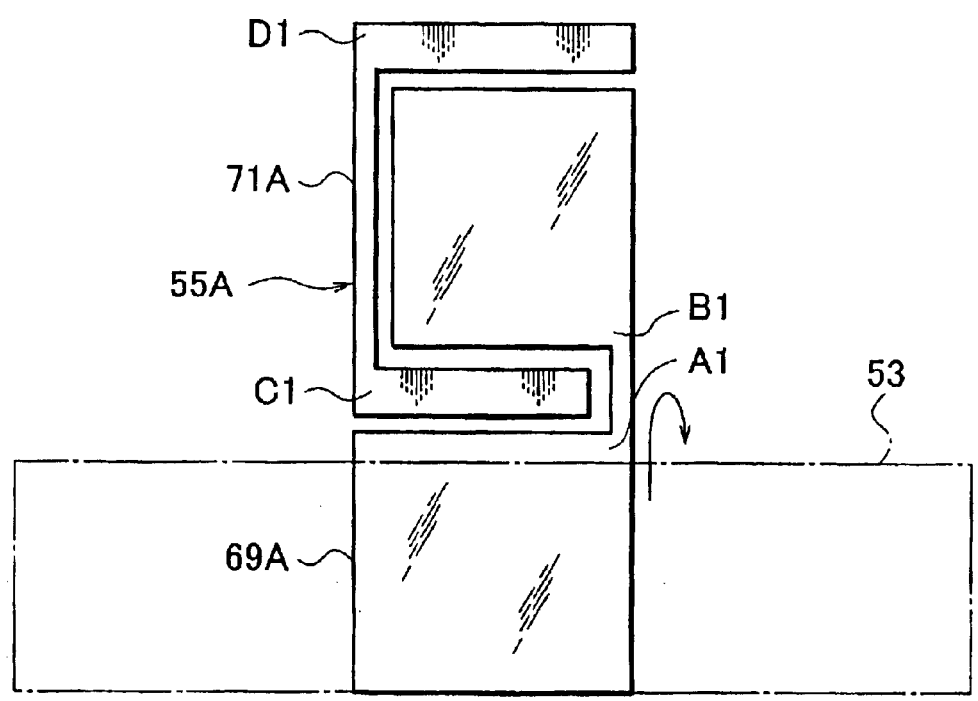
FIG. 6 is an explanatory view showing developed electrodes corresponding to the electrodes of FIG. 5.

FIG. 6 shows an electrode 55A equivalent to the electrode 55. The short-circuit points A, B, C, and D of the electrode 55 of FIG. 5 positionally correspond to points A1, B1, C1, and D1 of the electrode 55A of FIG. 6. With the parallelogram electrodes 69 and 71 and short-circuit points A, B, C, and D, the electrode 55 can spirally be wound around the cylinder 53.

In place of the electrode 55 of FIG. 5, the electrode 55A of FIG. 6 is employable for the sensor 19. In FIG. 6, the electrode 55A consists of a measuring electrode 69A and a ground electrode 71A that can be wound around the cylinder 53. The electrode 55 of FIG. 5 that is spirally wound around the cylinder 53 can more correctly and easily detect a capacitance change on the passage 1a than the electrode 55A of FIG. 6.

Figure 7:
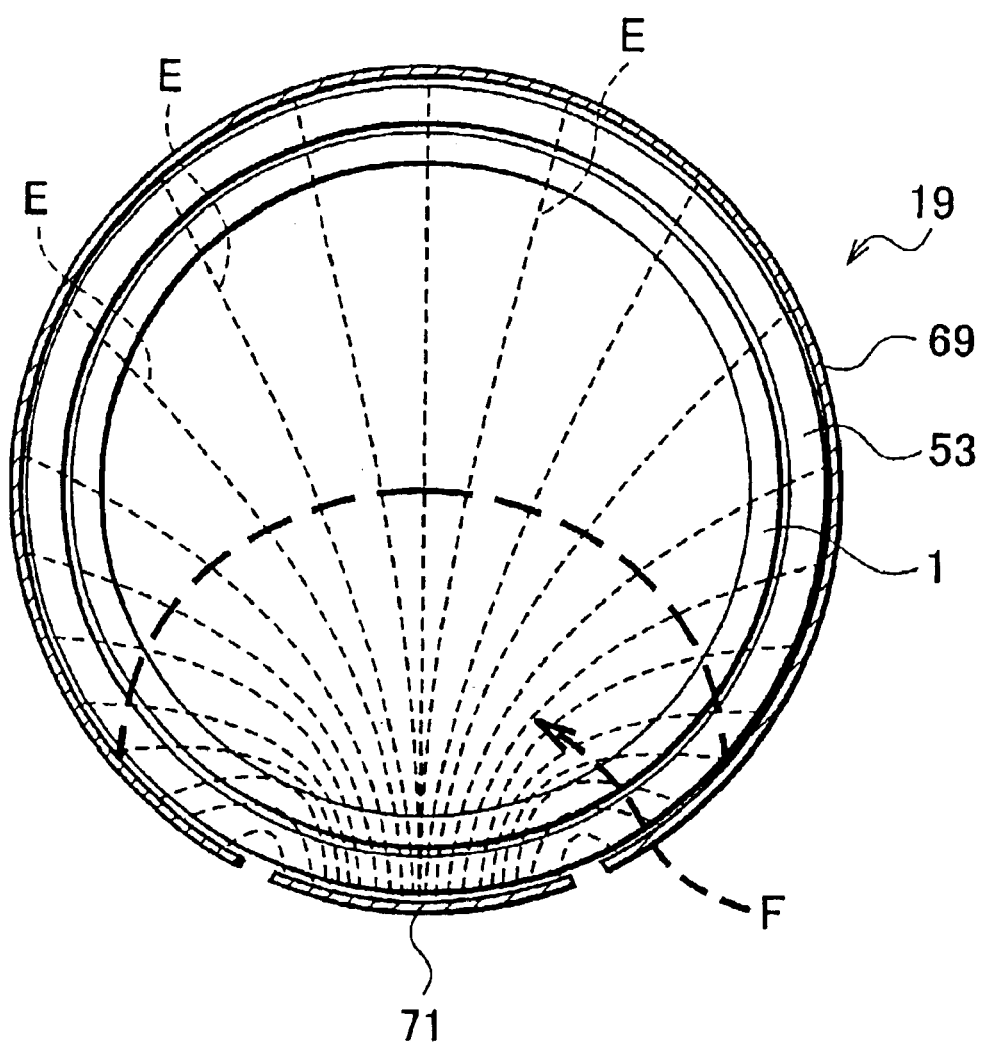
FIG. 7 is a schematic sectional view of the pipe with a ground electrode and measuring electrode of the sensor of FIG. 2.

FIG. 7 is a schematic sectional view of the pipe with a ground electrode and measuring electrode of the sensor of FIG. 2. In FIG. 7, the insulator 57 and the shield 59 are not shown. According to the sensor 19 serving as a capacitance sensor, the ground electrode 71 is narrower than the measuring electrode 69. Therefore, if the ground electrode 71 was positioned near the lower portion of the pipe 1, sensitivity-curved lines E forms a high sensitivity area F for the sensitivity-curved lines E in the lower portion of the pipe 1 adjacent to the ground electrode 71. Thus, when the ground electrode 71 and measuring electrode 69 are alternately disposed and are wound to be spiral along a flow direction, the high sensitivity area F is distributed around the circumference of the pipe 1 and formed in a 360 degree range. Accordingly, the sensor 19 can accurately make detection of capacitance of the pipe 1 with the high sensitivity area F formed in the 360 degree range.

Furthermore, a capacitance sensor with a ground electrode and measuring electrode having similar widths will have a relatively larger capacitance than the sensor 19 with the measuring electrode 69 of width substantially larger than the width of the ground electrode 71. As a result, the capacitance sensor with a ground electrode and measuring electrode having similar widths has a greater sensitivity to noise than the sensor 19 with the measuring electrode 69 of width substantially larger than the width of the ground electrode 71. Thus, the sensor 19 can make detection with greater accuracy.

Figure 8:
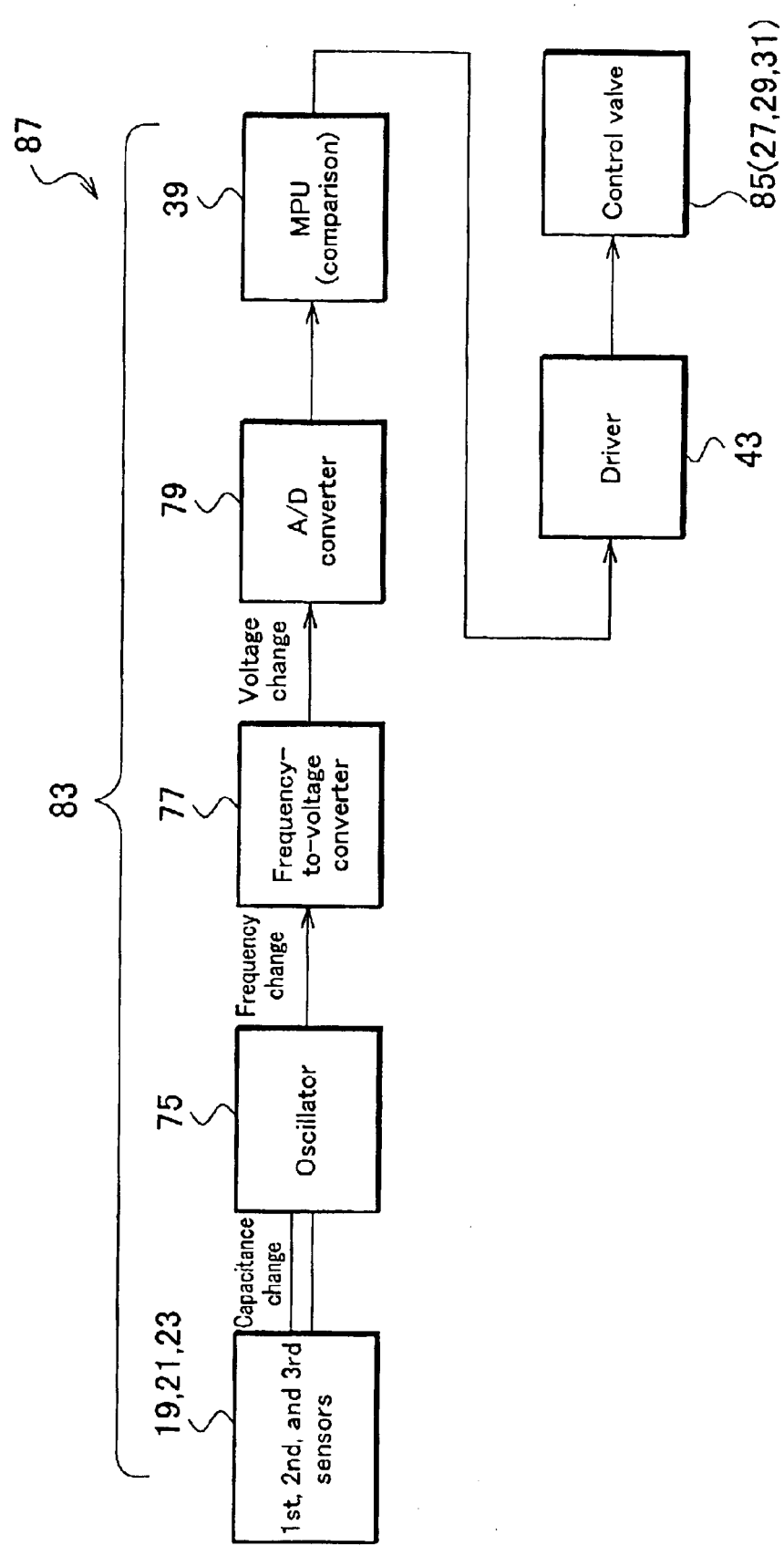
FIG. 8 is a block diagram showing the purity controller according to the first embodiment.

FIG. 8 is a block diagram showing the purity controller according to the first embodiment having the above-mentioned measuring function. The first to third sensors 19, 21, and 23, an oscillator 75, a frequency-to-voltage converter 77, an A/D converter 79, and the MPU 39 form an insulative fluid measuring apparatus 83. The measuring apparatus 83, the driver 43, and a control valve 85 (collectively representing the first to third solenoid valves 27, 29, and 31) form the purity controller 87.

A capacitance change detected by any one of the first to third sensors 19, 21, 23 is transferred to the oscillator 75, which provides a frequency change representative of the capacitance change. The frequency change is converted by the frequency-to-voltage converter 77 into a voltage change. The voltage change is converted by the A/D converter 79 into a digital binary signal. According to the digital binary signal, the MPU 39 compares the detected capacitance change with the reference capacitance changes.

According to the comparison result, the MPU 39 measures a ratio at the first sensor 19 of gas (bubbles) and silicon wafer fragments contained in the ultrapure water flowing through the passage 1a. The MPU 39 also measures a ratio at the second sensor 21 of gas (bubbles) contained in the ultrapure water flowing through the passage 1a. Further, the MPU 39 measures a ratio at the third sensor unit 23 of silicon wafer fragments contained in the ultrapure water flowing through the passage 1a.

As shown in FIG. 1, the passage 1a passes ultrapure water up to the outlet 7, and the first to third sensors 19, 21, and 23 detect capacitance changes on the passage 1a.

If gas (bubbles) is detected at the second sensor 21, the MPU 39 sends signals through the driver 43 to the first to third solenoid valves 27, 29, and 31, to close the first and third solenoid valves 27 and 31 and open the second solenoid valve 29. As a result, the ultrapure water containing the gas is guided through the first branch pipe 13 into the recycle tank 17.

If silicon wafer fragments are detected at the third sensor 23, the MPU 39 sends signals through the driver 43 to the first to third solenoid valves 27, 29, and 31, to close the first and second solenoid valves 27 and 29 and open the third solenoid valve 31. As a result, the ultrapure water containing the silicon wafer fragments is guided through the second branch pipe 15 into the recycle tank 17.

If no silicon wafer fragments are detected at the third sensor 23, the MPU 39 sends signals through the driver 43 to the first to third solenoid valves 27, 29, and 31, to close the second and third solenoid valves 29 and 31 and open the first solenoid valve 27. As a result, the ultrapure water containing no foreign matter is discharged from the outlet 7.

The ultrapure water from the outlet 7 is used to wash semiconductor silicon wafers without damaging the wafers. This results in greatly improving the yields of wafers.

After washing wafers, the ultrapure water is collected in the recycle tank 17, which forwards the ultrapure water to the regenerator 5. The regenerator 5 removes foreign matter such as silicon wafer fragments from the ultrapure water. The regenerated ultrapure water is supplied to the end 3 of the pipe 1 and into the passage 1a.

Detection results from the first and second sensors 19 and 21 are usable to determine the normality and maintenance/replacement timing of the filter 25.

Through the processes mentioned above, the first embodiment repeatedly use ultrapure water to wash semiconductor silicon wafers.

The first embodiment is capable of detecting the conditions of ultrapure water flowing through the passage 1a in a noncontact manner to cause no electrode corrosion, and therefore, is capable of surely maintaining the purity of the ultrapure water flowing through the passage 1a.

A capacitance change generates a large voltage change, and therefore, there is no need of integrating detected results. Consequently, the first embodiment involves a smaller number of computing operations, can quickly and correctly carry out control operations, and can minimize the size of the measuring apparatus.

The first embodiment measures a purity of ultrapure water from a capacitance change, and therefore, is hardly affected by a magnetic field. Consequently, the second and third sensors 21 and 23 can be installed in the vicinities of the first to third solenoid valves 27, 29, and 31. This improves the degree of freedom of designing the measuring apparatus.

Figure 9:
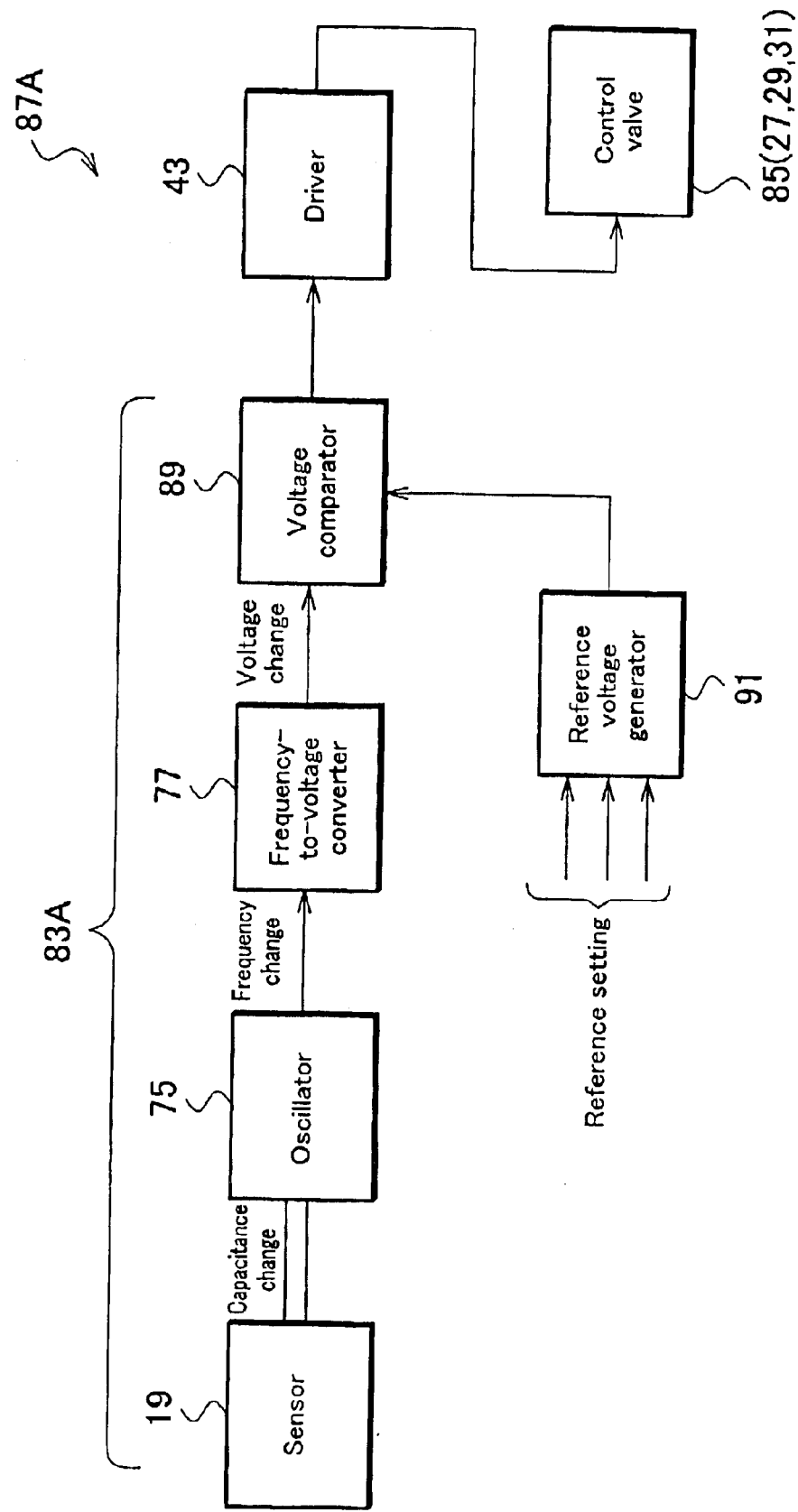
FIG. 9 is a block diagram showing a purity controller for an insulative fluid according to a modification of the first embodiment.

FIG. 9 shows a purity controller for an insulative fluid according to a modification of the first embodiment. The modification of FIG. 9 basically employs the same parts as those shown in FIGS. 1 and 7, which are represented with like reference numerals in FIG. 9. Only difference is that the purity controller 87A of FIG. 9 employs a voltage comparator 89 and a reference voltage generator 91 instead of the A/D converter 79 and MPU 39 of FIG. 8.

In FIG. 9, the first to third sensors 19, 21, and 23, oscillator 75, frequency-to-voltage converter 77, voltage comparator 89, and reference voltage generator 91 form a measuring apparatus 83A for an insulative fluid. The measuring apparatus 83A, the driver 43, and a control valve 85 (collectively representing the first to third solenoid valves 27, 29, and 31) form the purity controller 87A.

The reference voltage generator 91 generates reference voltages used for comparison by the voltage comparator 89. The reference voltages correspond to the reference capacitance changes 37. Accordingly, the reference voltage generator 91 serves as a reference storage unit.

The reference voltages generated by the reference voltage generator 91 are sent to the voltage comparator 89, which compares the reference voltages with a voltage representative of a detected capacitance change. According to the comparison result, the voltage comparator 89 provides signals to the control valves 27, 29, and 31 through the driver 43.

Like the first embodiment, the modification of FIG. 9 compares a voltage representative of a capacitance change with the reference values, controls the first to third solenoid valves 27, 29, and 31 accordingly, and provides suitable ultrapure water from the outlet 7.

According to the embodiment and modification mentioned above, the second branch pipe 15 is provided with the third solenoid valve 31. Instead, the first solenoid valve 27 may be a 3-way valve connected to the outlet 7 and second branch pipe 15. The 3-way valve is electrically controlled by the control unit 35, to switch a flow of ultrapure water to one of the outlet 7 and recycle tank 17.

According to the embodiment and modification, the first to third sensors 19, 21, and 23 are fitted to the linear pipe 1. Instead, the cylindrical insulators 53 and 57 and shield 59 may be made of soft materials so that they may easily be fitted to bends or corners of a pipe. In this case, the spirally wound electrode 55 is advantageous in arranging it around the bends or corners.

The electrode 55 or 55A may directly be wound around the pipe 1 made of, for example, vinyl chloride, to omit the cylinder 53. The cylinder 53 may be joined to the middle of the pipe 1 to form a part of the pipe 1.

(Second Embodiment)

Figure 10:
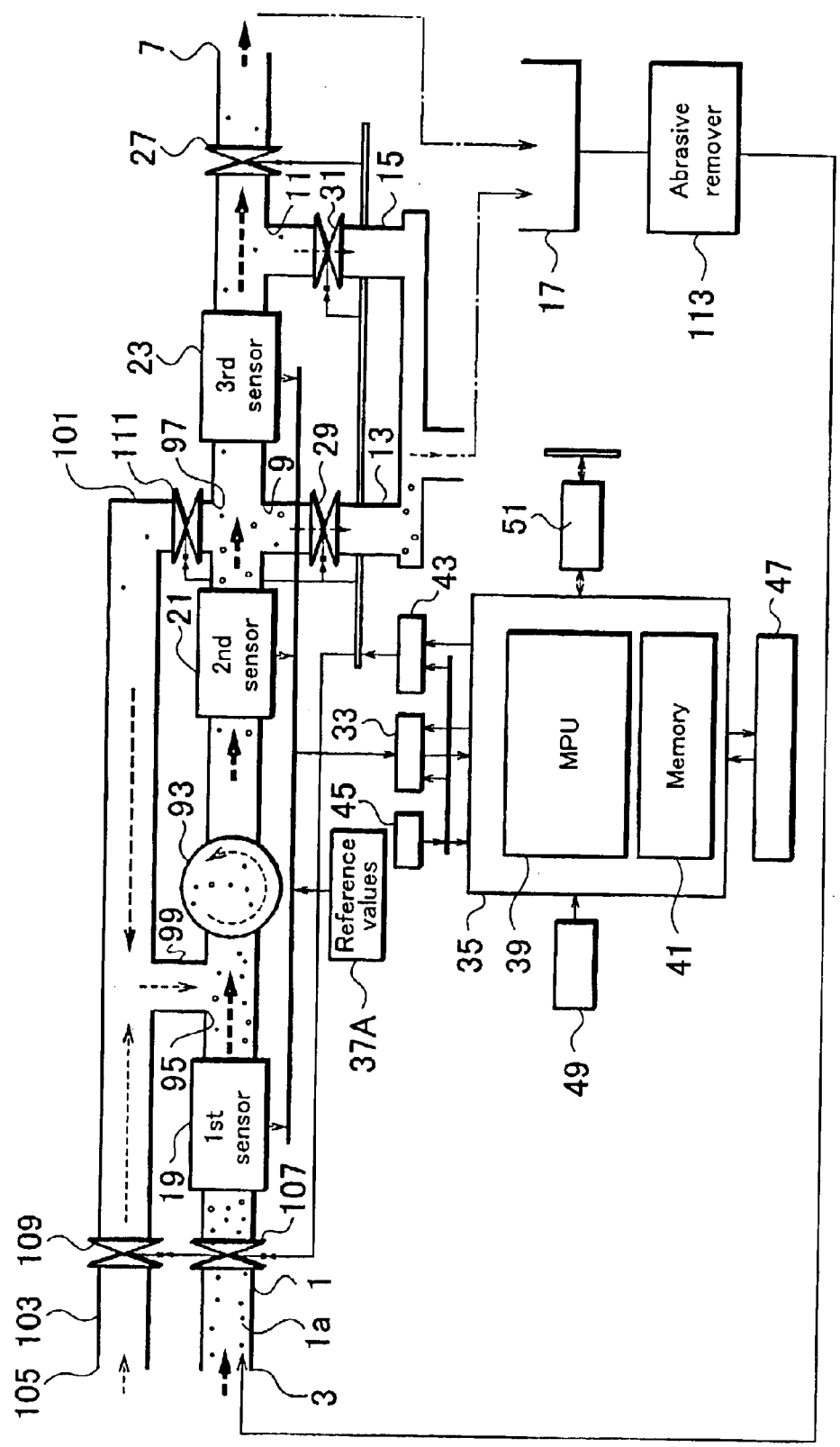
FIG. 10 is a schematic view showing a mixing ratio controller for an insulative fluid according to a second embodiment of the present invention.
Figure 11:
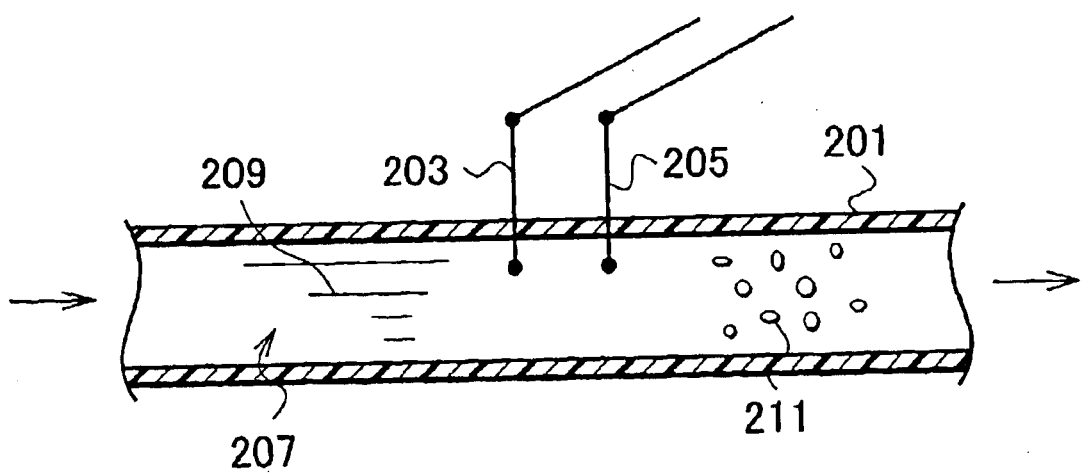
FIG. 11 is a schematic view showing a measuring apparatus for an insulative fluid according to a prior art.

FIG. 10 is a schematic view showing a mixing ratio controller for an insulative (nonconductive) fluid according to the second embodiment of the present invention. Parts corresponding to those of the first embodiment and modification are represented with like reference numerals.

The insulative fluid flowing through a pipe 1 (FIG. 2) according to the second embodiment is abrasive (slurry) used to mirror-finish, for example, semiconductor silicon wafers. The slurry is a mixture of ultrapure water and silica particles of several millimicrons. The silica is a kind of aluminum ceramics.

Instead of the filter 25 and regenerator 5 of FIG. 1, the second embodiment of FIG. 10 employs a mixer 93 and an abrasive remover 113. The mixer 93 mixes at least two kinds of insulative fluids with each other and pours the mixed fluids into a passage 1a. According to the second embodiment, the mixer 93 mixes ultrapure water with silica particles.

The pipe 1 has a confluent mouth 95 upstream of the mixer 93 and a circulation mouth 97 downstream of a second sensor 21. The confluent mouth 95 is connected to a confluent pipe 99, and the circulation mouth 97 is connected to a circulation pipe 101. The confluent pipe 99 and circulation pipe 101 are connected to an ultrapure water supply pipe 103. Ultrapure water is supplied to the pipe 103 thorough an end 105 thereof.

In the vicinity of an end 3 of the pipe 1, there is a first sensor 19. Upstream of the first sensor 19, there is a fourth solenoid valve 107. In the vicinity of the end 105 of the supply pipe 103, there is a fifth solenoid valve 109. The circulation pipe 101 has a sixth solenoid valve 111.

A control unit 35 stores a reference capacitance change 37A corresponding to a proper concentration of slurry flowing through the passage 1a toward an outlet 7.

Like the first embodiment, the control unit 35 serves as a ratio measuring unit to compare capacitance changes detected by the first to third sensors 19, 21, and 23 with reference capacitance changes stored in a memory 41 and measure a ratio related to the slurry flowing through the passage 1a. According to the comparison result, the control unit 35 determines whether or not the slurry flowing through the passage 1a has a proper concentration. The control unit 35 measures a mixing ratio of the slurry, i.e., a mixing ratio of silica particles to ultrapure water flowing through the passage 1a.

The control unit 35 controls the first, second, third, and sixth solenoid valves 27, 29, 31, and 111 such that, if the measured mixing ratio is within a set value, the slurry flowing through the passage 1a is guided to the outlet 7, and if the measured mixing ratio is out of the set value, to one of the first and second branch mouths 9 and 11 and circulation mouth 97. To achieve this, the control unit 35 is connected through a driver 43 to the solenoid valves 27, 29, 31, and 111.

The driver 43 is connected to the fourth and fifth solenoid valves 107 and 109 to control the supply of slurry and ultrapure water.

The mixing ratio controller according to the second embodiment may have a structure similar to any one of those shown in FIGS. 8 and 9. In this case, one of the purity controllers 87 and 87A of FIGS. 8 and 9 serves as the mixing ratio controller.

In FIG. 10, slurry with silica particles is supplied to the end 3 of the passage 1a, and ultrapure water is supplied as and when required to the end 105 of the supply pipe 103. The supply of slurry is adjusted by the control unit 35 by controlling the fourth solenoid valve 107. The supply of ultrapure water is adjusted by the control unit 35 by controlling the fifth solenoid valve 109.

The supplied ultrapure water is passed through the confluent pipe 99 and confluent mouth 95 to the pipe 1. The ultrapure water, slurry, and silica particles are mixed with one another by the mixer 93 and are passed through the second sensor 21.

If, at the second sensor 21, it is determined that a concentration of the slurry is lower than a reference level, the control unit 35 opens the sixth solenoid valve 111 to return the low-concentration slurry through the circulation pipe 101 to the confluent pipe 99. If, at the second sensor 21, the slurry concentration is high, the control unit 35 opens the second solenoid valve 29 to pass the high-concentration slurry through a first branch pipe 13 to a recycle tank 17.

If, at the second sensor 21, the slurry concentration is appropriate, the slurry is passed through the third sensor 23. If, at the third sensor 23, semiconductor silicon wafer fragments are detected in the slurry, the control unit 35 opens the third solenoid valve 31 to pass the slurry containing the silicon wafer fragments through a second branch pipe 15 to the recycle tank 17.

If, at the third sensor 23, the slurry contains no silicon wafer fragments and has a proper concentration, the control unit 35 opens the first solenoid valve 27 to discharge the slurry containing no silicon wafer fragments and having a proper concentration through the outlet 7.

The slurry from the outlet 7 with a proper concentration is used to correctly mirror-finish semiconductor silicon wafers without damaging the wafers. This results in improving the yields of semiconductor products.

The slurry used to polish silicon wafers is collected in the recycle tank 17, which transfers the slurry to the abrasive remover 113. The abrasive remover 113 regenerates the slurry by removing silicon wafer fragments and the like from the slurry and supplies the regenerated slurry to the end 3 of the pipe 1.

Through these processes, the slurry is repeatedly used to polish semiconductor silicon wafers.

Consequently, the second embodiment provides the same effects as the first embodiment. In addition, the second embodiment can correctly polish semiconductor silicon wafers with slurry containing no unwanted matter and having a proper concentration, to improve the yields of semiconductor products.

The second embodiment is applicable to mix three or more kinds of insulative fluids.

Any one of the embodiments can compare capacitance values themselves instead of capacitance changes with reference capacitance values. The first to third sensors 19, 21, and 23 may be arranged in the pipe 1. The first and third solenoid valves 27 and 31 are replaceable with a 3-way valve. It is possible to employ one of the second and third sensors 21 and 23 instead of the two.

What is claimed is:

1. A measuring apparatus for an insulative fluid, comprising:
   a capacitance sensor for sensing a detected capacitance change on in a passage, through which said insulative fluid is flowing, said capacitance sensor comprising:
   a measuring electrode, and
   a ground electrode, narrower than, spaced apart from, and paired with said measuring electrode;
   with said measuring electrode and said ground electrode wound around said passage in a spiral, such that said spiral is oriented in a direction of flow of said insulative fluid;
   a storage unit for storing a reference capacitance change; and
   a ratio measuring unit for comparing the detected capacitance change with the reference capacitance change and for determining a ratio related to the insulative fluid flowing through the passage.

2. The measuring apparatus of claim 1, wherein:
   the ratio measuring unit measures a purity of said insulative fluid flowing through said passage.

3. The measuring apparatus of claim 2, further comprising:
   a filter, positioned upstream of said capacitance sensor, for removing foreign matter from the insulative fluid flowing through the passage;
   an outlet, and a branch mouth, both arranged downstream of said filter;
   an adjuster, for switching the flow of the insulative fluid to one of said outlet and said branch mouth; and
   a controller, for controlling the adjuster to switch the flow of the insulative fluid to said outlet if the measured purity is within a set value, and to said branch mouth, if the measured purity is out of the set value.

4. The measuring apparatus of claim 1, wherein:
   the ratio measuring unit measures a mixing ratio of said insulative fluid flowing through said passage.

5. The measuring apparatus of claim 4, further comprising:
   a mixer, for mixing at least two kinds of insulative fluids with each other, and for pouring the mixed insulative fluids into said passage;
   an outlet, and a branch mouth, both arranged downstream of the mixer;
   an adjuster for switching the flow of the mixed insulative fluids to one of sid outlet and said branch mouth; and
   a controller, for controlling the adjuster to switch the flow of the mixed insulative fluids to the outlet, if the measured mixing ratio is within a set value, and to the branch mouth, if the measured mixing ratio is out of the set value.

* * * * *